(12) United States Patent
Garon et al.

(10) Patent No.: US 9,381,330 B2
(45) Date of Patent: Jul. 5, 2016

(54) DRAIN CATHETER

(71) Applicant: Corporation de l'École Polytechnique de Montréal, Montreal (CA)

(72) Inventors: Andre Garon, Anjou (CA); Michel Carrier, Montreal (CA)

(73) Assignees: Michel Carrier, Montréal (CA); POLYVALOR, LIMITED PARTNERSHIP, Montréal (CA)

( * ) Notice: Subject to any disclaimer, the term of this patent is extended or adjusted under 35 U.S.C. 154(b) by 231 days.

(21) Appl. No.: 13/918,181

(22) Filed: Jun. 14, 2013

(65) Prior Publication Data

US 2013/0345679 A1 Dec. 26, 2013

Related U.S. Application Data

(60) Provisional application No. 61/659,504, filed on Jun. 14, 2012.

(51) Int. Cl.
*A61M 27/00* (2006.01)
*A61M 25/14* (2006.01)
(Continued)

(52) U.S. Cl.
CPC ........... *A61M 27/00* (2013.01); *A61M 25/0069* (2013.01); *A61M 25/0071* (2013.01);
(Continued)

(58) Field of Classification Search
CPC ............ A61M 25/0069; A61M 27/00; A61M 25/0071; A61M 25/0068; A61M 25/0067; A61M 2025/004; A61M 2025/0037; A61M 2025/0034; A61M 25/003; A61M 25/0029; A61M 25/0026; A61M 25/0023; A61M 25/0021; A61M 25/00; A61M 1/0086; A61M 1/008; A61M 1/0064; A61M 1/0058; F16L 59/021; F16L 59/022; F16L 59/024; F16L 59/025; F16L 17/04; H02G 15/013; H02G 3/0616; H02G 3/0625; H02G 3/083
USPC .......................... 285/331, 354, 355, 388, 389
See application file for complete search history.

(56) References Cited

U.S. PATENT DOCUMENTS 1,851,940 A * 3/1932 Williams ......................... 138/89
4,072,153 A * 2/1978 Swartz .................. A61M 27/00
604/284
(Continued)

OTHER PUBLICATIONS

Three Inscribed Circles Into Big Circle. Math Help Forum. Oct. 5, 2008. http://mathhelpforum.com/geometry/52213-three-inscribed-circles-into-big-circle.html.*

*Primary Examiner* — Adam Marcetich
(74) *Attorney, Agent, or Firm* — Norton Rose Fulbright Canada LLP

(57) ABSTRACT

A drain catheter comprises a proximal drain tube having a proximal end adapted to outlet drained liquids and a distal end. A tube interface is at a distal end of the proximal drain tube, the tube interface having at least two canals open to a distal end of the proximal drain tube, the at least two canals being in fluid communication with the proximal drain tube. Two or more distal drain tubes each having a proximal end and a distal end, the proximal end of each said distal drain tube being connected to a corresponding one of the canals such that the distal drain tubes are each in fluid communication with the corresponding one of the canals, the distal end of each said distal drain tube being open to collect liquids, a lumen of the distal drain tubes being smaller than a lumen of the proximal drain tube.

15 Claims, 5 Drawing Sheets

(51) Int. Cl.
*A61M 1/00* (2006.01)
*A61M 25/00* (2006.01)

(52) U.S. Cl.
CPC ............ *A61M1/008* (2013.01); *A61M 25/0014* (2013.01); *A61M 25/0097* (2013.01); *A61M 2025/004* (2013.01); *A61M 2025/0034* (2013.01); *A61M 2025/0036* (2013.01)

(56) References Cited

U.S. PATENT DOCUMENTS

| | | | | |
|---|---|---|---|---|
| 4,465,481 A | * | 8/1984 | Blake | 604/541 |
| 4,622,436 A | * | 11/1986 | Kinnan | 174/77 R |
| 4,801,158 A | * | 1/1989 | Gomi | 285/52 |
| 4,838,881 A | * | 6/1989 | Bennett | A61M 25/009 156/294 |
| 5,100,395 A | * | 3/1992 | Rosenberg | A61M 1/0005 604/247 |
| 5,254,084 A | * | 10/1993 | Geary | A61M 1/285 604/29 |
| 5,266,743 A | * | 11/1993 | Helbawi | 174/93 |
| 5,290,073 A | * | 3/1994 | Chen | 285/149.1 |
| 5,458,582 A | * | 10/1995 | Nakao | A61M 25/007 604/264 |
| 5,775,702 A | * | 7/1998 | Laeremans et al. | 277/314 |
| 5,891,111 A | * | 4/1999 | Ismael | 604/541 |
| 6,066,090 A | * | 5/2000 | Yoon | A61B 1/00045 600/113 |
| 7,015,394 B2 | * | 3/2006 | Desard et al. | 174/100 |
| 8,628,091 B2 | * | 1/2014 | Davison | 277/314 |
| 2005/0159697 A1 | * | 7/2005 | Dextradeur et al. | 604/8 |
| 2006/0042814 A1 | * | 3/2006 | Ball et al. | 174/65 G |
| 2009/0018493 A1 | * | 1/2009 | Ash | A61M 1/284 604/29 |
| 2014/0088567 A1 | * | 3/2014 | Nieman et al. | 604/533 |

* cited by examiner

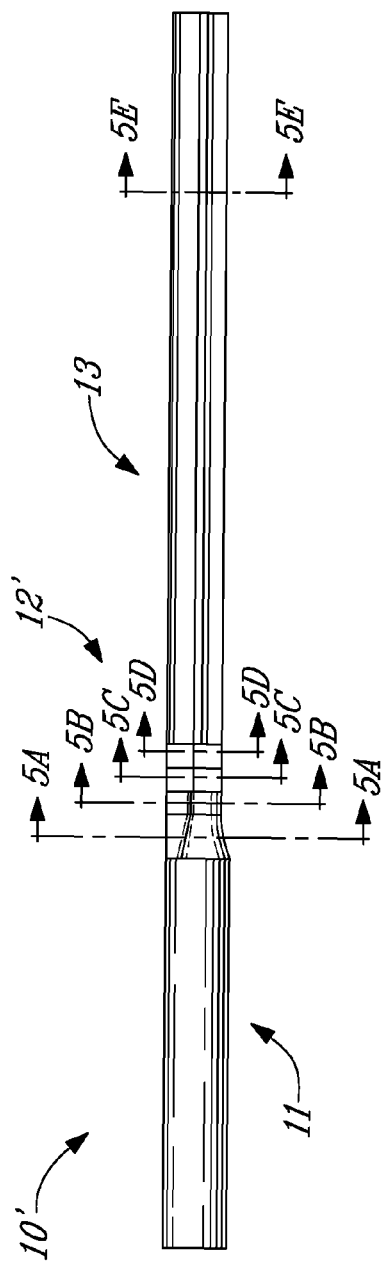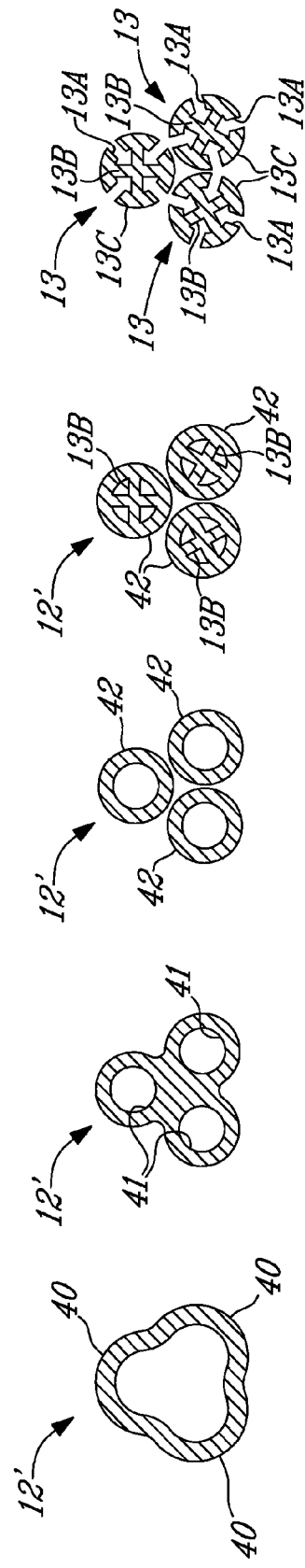

DRAIN CATHETER

CROSS-REFERENCE TO RELATED APPLICATION

The present invention claims priority on U.S. Provisional Application Ser. No. 61/659,504, filed on Jun. 14, 2012, and incorporated herewith by reference.

TECHNICAL FIELD

The present invention relates to drain catheters for draining fluids from a body cavity, such as various cavities within the mediastinum.

BACKGROUND OF THE INVENTION

Drain catheters are commonly used for the drainage of bodily cavity. For instance, cavities in the mediastinum may require drainage subsequent to surgery, to avoid complications such as pericardial effusion. It is known to bundle a few small drain catheters and insert them concurrently through a blood vessel, whereby the drain catheter inlets of the bundle are spread out in the cavity that must be drained. However, the performance of some prior art drains may be affected by bodily debris (e.g., clots, etc). Indeed, the size of catheters is limited by blood vessel dimensions, and drain catheters of smaller diameter may become clogged. Moreover, the frictional forces in drain catheters of smaller diameter are also relatively high compared to drain catheters with a greater lumenal area.

SUMMARY

It is therefore an aim of the present disclosure to provide a drain catheter that addresses issues related to the prior art.

Therefore, in accordance with a first embodiment, there is provided a drain catheter comprising: a proximal drain tube having a proximal end adapted to outlet drained liquids and a distal end; a tube interface at a distal end of the proximal drain tube, the tube interface having at least two canals open to a distal end of the proximal drain tube, the at least two canals being in fluid communication with the proximal drain tube; and at least two distal drain tubes each having a proximal end and a distal end, the proximal end of each said distal drain tube being connected to a corresponding one of the canals such that the distal drain tubes are each in fluid communication with the corresponding one of the canals, the distal end of each said distal drain tube being open to collect liquids, a lumen of the distal drain tubes being smaller than a lumen of the proximal drain tube.

BRIEF DESCRIPTION OF THE DRAWINGS

FIG. 4 is a longitudinal view of drain catheter in accordance with an embodiment of the present disclosure;

FIGS. 5A to 5E are cross-sectional views of the drain catheter of FIG. 4, taken at various locations along the drain catheter.

DETAILED DESCRIPTION OF THE EMBODIMENTS

Figure 1:
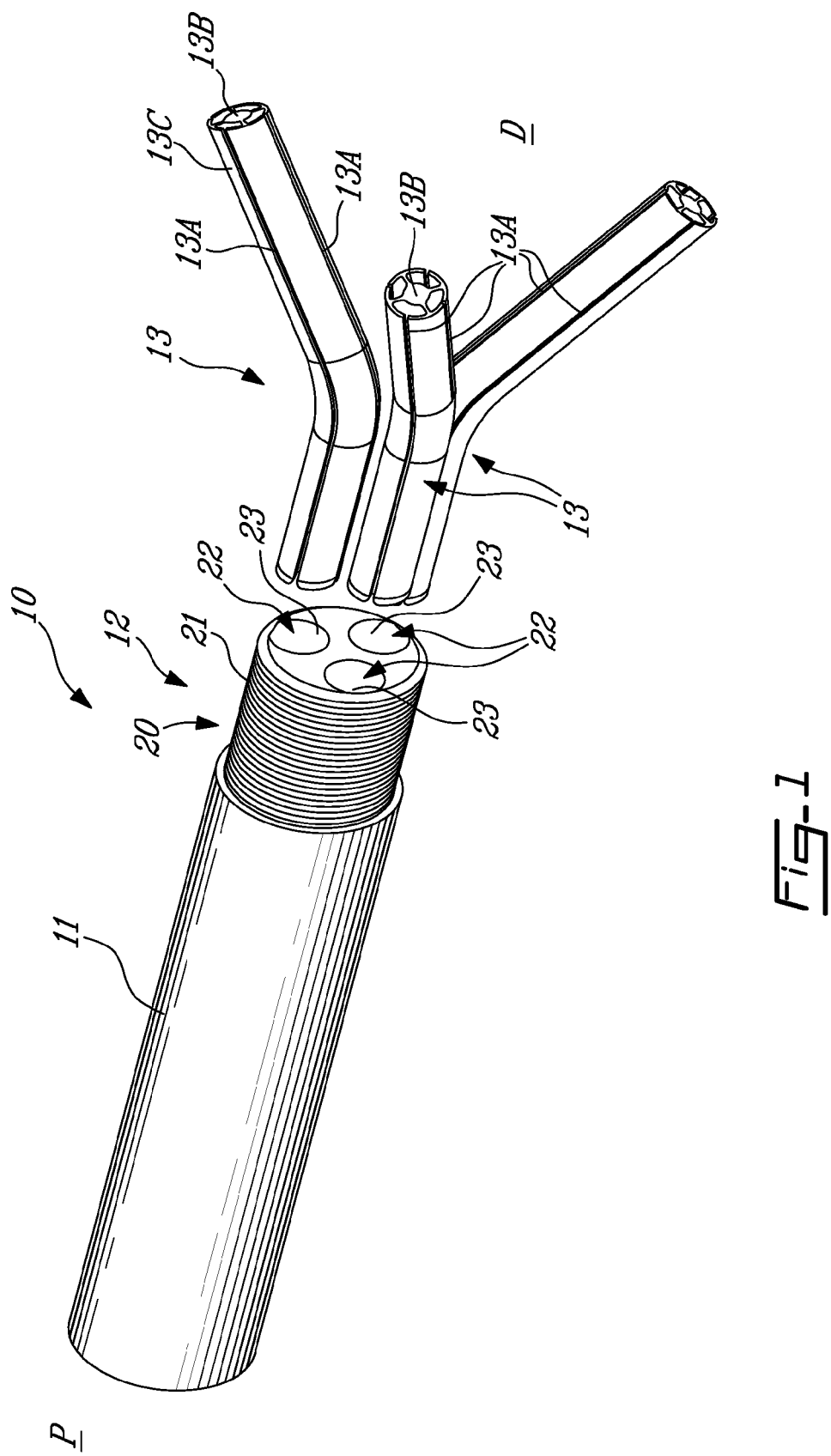
FIG. 1 is an assembly view of a drain catheter in accordance with an embodiment of the present disclosure.

Referring to the drawings and more particularly to FIG. 1, a drain catheter in accordance with the present disclosure is generally shown at 10. The drain catheter 10 is used for the drainage of bodily fluids from body cavities. For instance, the drain catheter 10 may be used for the drainage of fluid from cavities within the mediastinum, for instance after cardiac surgery. Hence, the drain catheter 10 has a proximal end located outside the body, and a distal end within the body, with the longitudinal body of the drain catheter 10 within a body vessel.

The drain catheter 10 has a main proximal drain tube 11, a tube interface 12 and two or more distal drain tubes 13. For clarity purposes, the main proximal drain tube 11 is relatively short in FIG. 1 (e.g., fragmented), but may have a substantial length relative to its outer diameter, to extend out of the body. Moreover, the length of the main proximal drain tube 11 may be substantially greater than the length of each distal drain tube 13. The tube interface 12 may be in or out of the body while the distal drain tubes 13 are mostly, if not fully, within the body. The end of the main proximal drain tube 11 located outside the body at end P is configured to be connected to any suitable suction source, fluid collection system, drainage device or accessory, while the free ends of the distal drain tubes 13 at end D of the drain catheter 10 are distributed at various locations of a body cavity to drain. Various types of connectors may be located at the proximal end P of the main proximal drain tube 11. Any appropriate medical grade material may be used for the main proximal drain tube 11. For instance, a silicone such as Silastic® of Rx type may be used, with the hardness being selected as a function of the contemplated use, to sustain suction pressures in the range of 20 cm $H_2O$ without collapsing.

The tube interface 12 is inserted into a distal-most end of the main proximal drain tube 11. The tube interface 12 is the interface between the main proximal drain tube 11 and the plurality of distal drain tubes 13. The tube interface 12 is connected to the main proximal drain tube 11. The tube interface 12 may be sealingly connected to the main proximal drain tube 11, so as to minimize pressure lost at the junction between the tube interface 12 and the main proximal drain tube 11. The tube interface 12 is described in further details hereinafter.

Still referring to FIG. 1, there is illustrated three of the distal drain tubes 13. The drain catheter 10 has two or more of the distal drain tubes 13. The amount of distal drain tubes 13 is limited by the minimal dimensions of the distal drain tubes 13: i.e., depending on the application, a minimal diameter is required for the distal drain tubes 13 to operate efficiently. According to an embodiment, each of the distal drain tubes 13 is a multi-lumen catheter tube having longitudinal channels 13A extending the full length of the distal drain tube 13 to maximize the amount of fluid captured by the drain tubes 13, with a central cross-shaped core 13B extending along the distal drain tubes 13 to provide structural integrity to the distal drain tubes 13, and to support the elongated peripheral wall portions 13C forming the outer periphery of the distal drain tubes 13. The assembly of the central cross-shaped core 13B and the elongated peripheral wall portions 13C defines conduits within the drain tube 13. For instance, the distal drain tubes 13 may be similar to the flexible drain portion described in U.S. Pat. No. 4,398,910, granted to Blake et al. on Aug. 16, 1983. Other distal drain tube configurations are considered as well, with more or fewer of the longitudinal channels 13A. For instance, perforated tubes and like other tubes may be used. To minimize any pain sustained by the patient, the distal drain tubes 13 are made of a flexible and resilient material, such as silicone.

Figure 2:
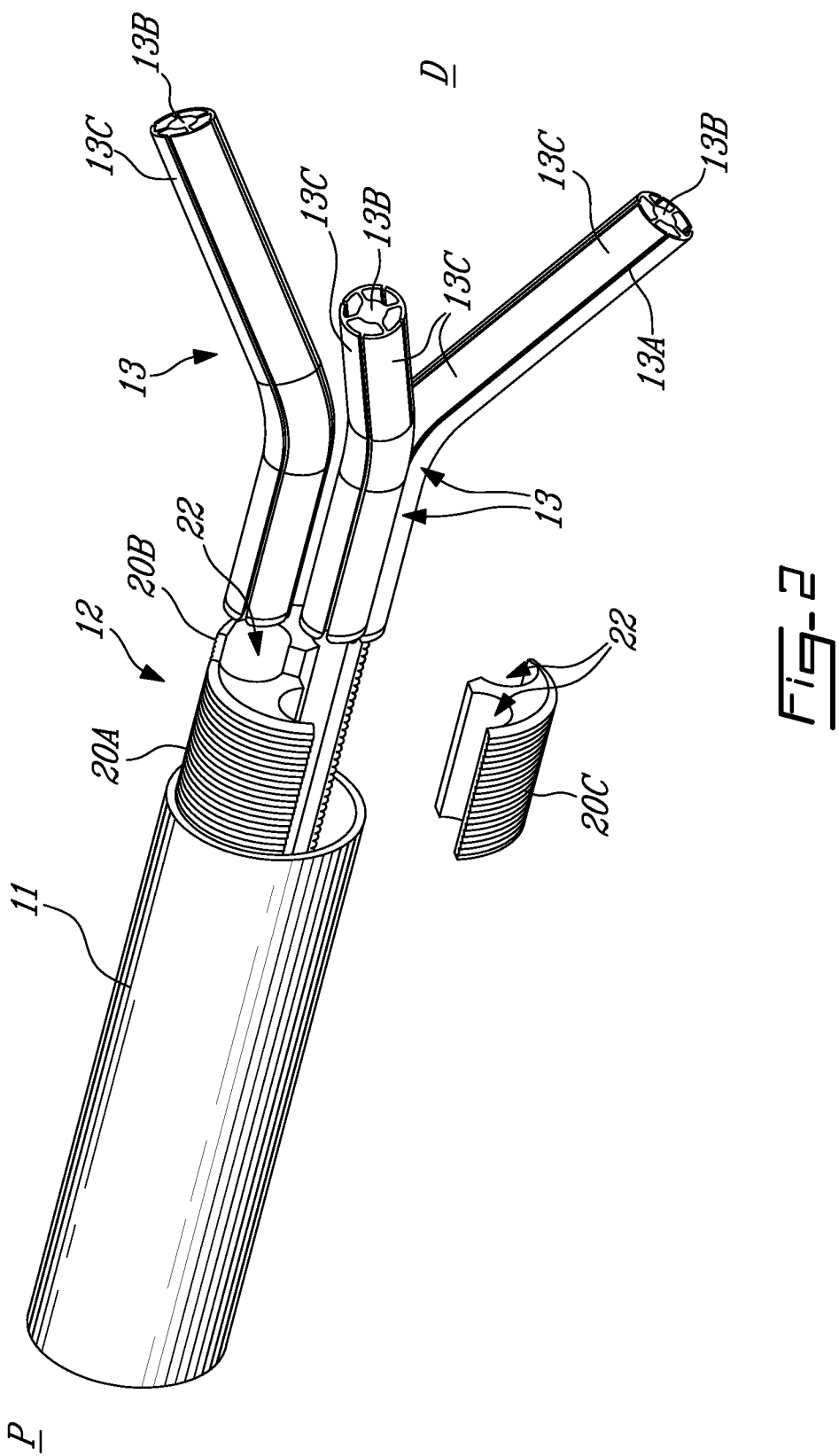
FIG. 2 is an assembly view of the drain catheter of FIG. 1, featuring interface body portions.

Referring to FIG. 1, the tube interface 12 is shown having a cylindrical body 20 shaped to fill the interstitial space between the inner diameter of the proximal drain tube 11 and the outer diameters of the distal drain tubes 13, in a generally airtight arrangement. Referring to FIG. 2, the cylindrical body 20 may consist of a plurality of cylindrical body portions 20A, 20B and 20C. The number of body portions is generally equivalent to the number of distal drain tubes 13. For instance, if the drain catheter 10 has two distal drain tubes 13, the tube interface 12 has two cylindrical body portions concurrently forming the cylindrical body 20.

An outer diameter 21 of the cylindrical body 20 is sized so as to be received in the distal-most end of the main proximal drain tube 11. Any appropriate type of interconnection between the tube interface 12 and the main proximal drain tube 11 is considered, such as a deformation fit, with or without the use of adhesives, etc. Referring to FIGS. 1 and 2, the cylindrical body 20 has canals 22 that will each receive a distal drain tube 13. Accordingly, the cylindrical body 20 has the same number of canals 22 as of distal drain tubes 13. In another embodiment, the canals 22 converge to a single canal at a proximal end of the tube interface 12. An inner diameter 23 (i.e., lumen) of each of the canals 22 is sized to accommodate a proximal-most end of the distal drain tubes 13, with the distal drain tubes 13 extend freely beyond the tube interface 12. The assembly of the distal drain tubes 13 to the tube interface 12, and of the tube interface 12 to the main proximal drain tube 11 is strong enough that these components remain connected to each other when the drain catheter 10 is pulled out of the body, despite frictional forces of the drain catheter with surrounding bodily tissue.

The cylindrical body 20 is made of a medical grade material. According to an embodiment, the cylindrical body 20 is made from silicone, with a non-negligible level of resiliency. One type of silicone that may be used is Silastic® of Rx type. In an embodiment, it is considered to use the same material for the distal drain tube 13, although differing materials may be used as well. According to an embodiment, the cylindrical body 20 has a greater rigidity than the distal drain tubes 13.

With reference to FIG. 2, the cylindrical body portions 20A, 20B and 20C are assembled onto the proximal-most ends of the distal drain tubes 13. This ensures that the peripheral material of the canals 22 properly covers the ends of the distal drain tubes 13 and therefore produces a generally fluid-tight joint. In assembling the distal drain tubes 13 to the tube interface 12, the length of the distal drain tubes 13 is adjusted by the user. The assembly of the cylindrical body portions 20A, 20B and 20C capturing the ends of the distal drain tubes 13 may then be inserted in the main proximal drain tube 11, using any appropriate type of manufacturing. For instance, the main proximal drain tube 11 may be resiliently deformed to insert the assembly therein.

Figure 3:
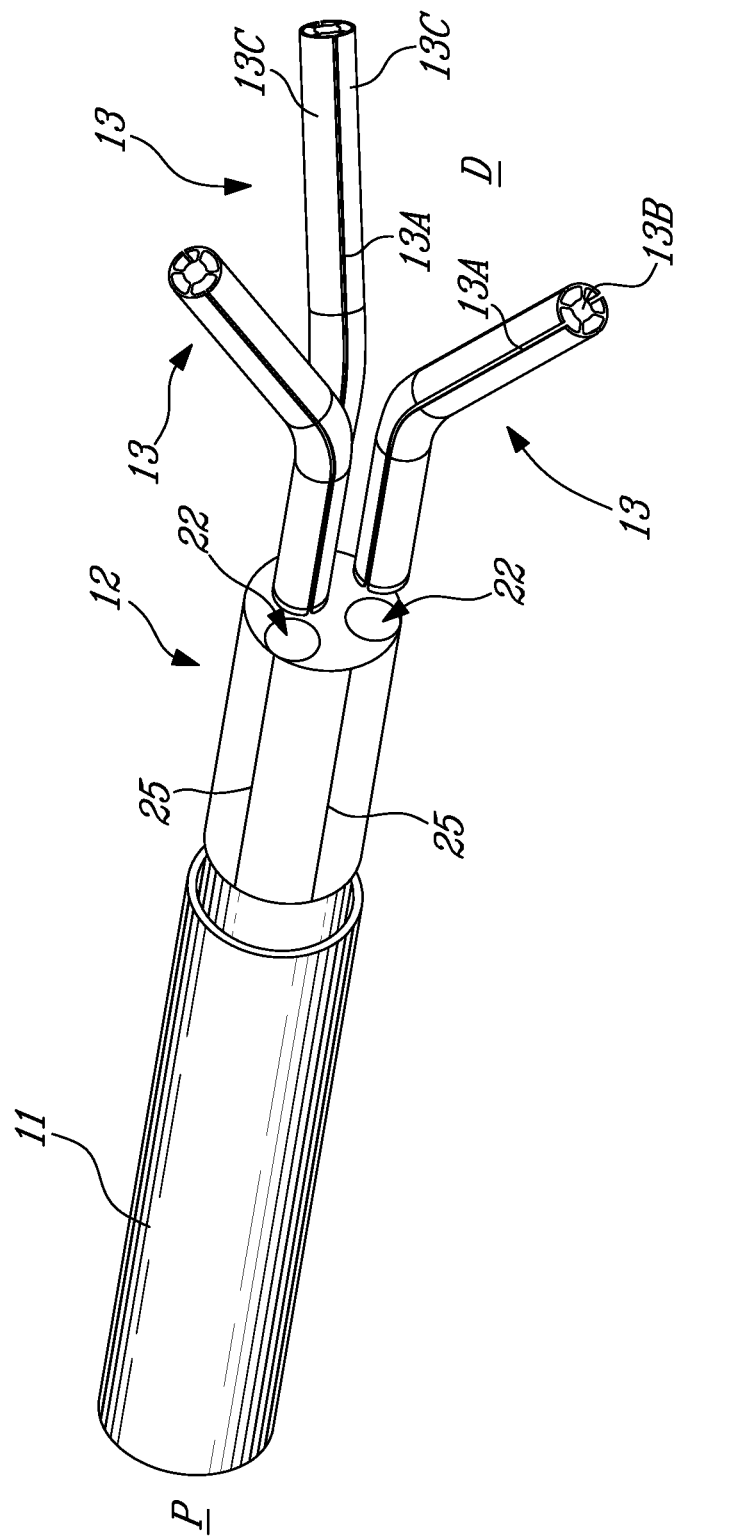
FIG. 3 is an assembly view of the drain catheter of FIG. 1, with longitudinal slits in a tube interface.

Referring to FIG. 3, an alternative embodiment of the tube interface 12 is shown, with the cylindrical body 20 having slits 25 in communication with each of the canals 22. In an embodiment, the slits 25 extend the full length of the canals 22. In the natural state of the cylindrical body 20, the slits 25 are closed by the resilience of the material of the cylindrical body 20. The slits 25 may however be manually opened for the insertion therein of the distal drain tubes 13. Once the distal drain tubes 13 are inserted in the tube interface 12 (with an appropriate length of the tubes 13 extending beyond the interface 12), the assembly may be inserted in the distal-most end of the main proximal drain tube 11.

It is observed that total frictional forces per volume of fluid are relatively lower for fluids circulating in the main proximal drain tube 11 with its single lumen, over the frictional forces for fluids in the plurality of distal drain tubes 13. Hence, the drain catheter 10 benefits from the lower frictional forces of the main proximal drain tube 11 for a substantial portion of the overall length of the drain catheter 10. Therefore, instead of having a plurality of tubes extending from an exterior of the body to the drained cavity, the use of a single proximal drain tube of greater lumenal dimensions connected to a plurality of distal drain tubes of smaller lumenal dimensions enhances the drainage of fluid. Moreover, by using distal drain tubes 13 having longitudinal grooves 13A extending proximally to the tube interface 12 and to the main proximal tube 11, as in FIG. 1, the distal drain tubes 13 expose substantial drainage area to drain fluids from the bodily cavities. This may reduce the risk of clogging the various tubes.

It is observed that the drain catheter 10 has a circular cross-sectional area. However, the drain catheter 10 may have any appropriate cross-sectional shapes (oval, etc), depending on the use of the drain catheter 10.

Referring to FIGS. 4 and 5A-5E, the drain catheter is shown at 10' in accordance with another embodiment of the present disclosure. The drain catheter 10' is similar to the drain catheter 10 shown in FIGS. 1-3, whereby like elements will bear like reference numerals. One difference between the drain catheters 10 and 10' is the interface portion 12' of the catheter 10' between the main proximal tube 11 and the distal drain tubes 13.

More specifically, referring concurrently to FIGS. 4 and 5E, it is observed that the drain catheter 10' has the main proximal tube 11 with a circular cross-section (although other section shapes are considered). The circular cross-section is well suited for the connected of the main proximal tube 11 to a suction source. The distal drain tubes 13 have the longitudinal channels 13A, the central cross-shaped cores 13B, and the resulting conduits extending along the drain tubes 13.

The drain catheter 10' is a single integral molded piece that may have an edgeless outer surface, with the interface portion 12' being the transition between the circular shape of the main proximal tube to the specific shape of the distal drain tubes 13 as shown in FIG. 5E. Hence, as shown in FIG. 5A, the interface portion 12' has three lobes 40. The number of lobes is in accordance with the number of distal drain tubes 13. As shown in FIG. 5B, the interface portion 12' transitions from the three-lobe configuration of FIG. 5A, to a configuration of three conduits 41 of circular inner diameter. As shown in FIG. 5C, the three interconnected conduits 41 of FIG. 5B detach to form three individual tubes 42, having a diameter generally corresponding to that of the distal drain tubes 13. Then, sequentially to FIG. 5D, the tubes 42 of FIG. 5C feature the central cross-shaped core 13B, but without the longitudinal channels 13A, to then reach the configuration of FIG. 5E.

Figure 6:
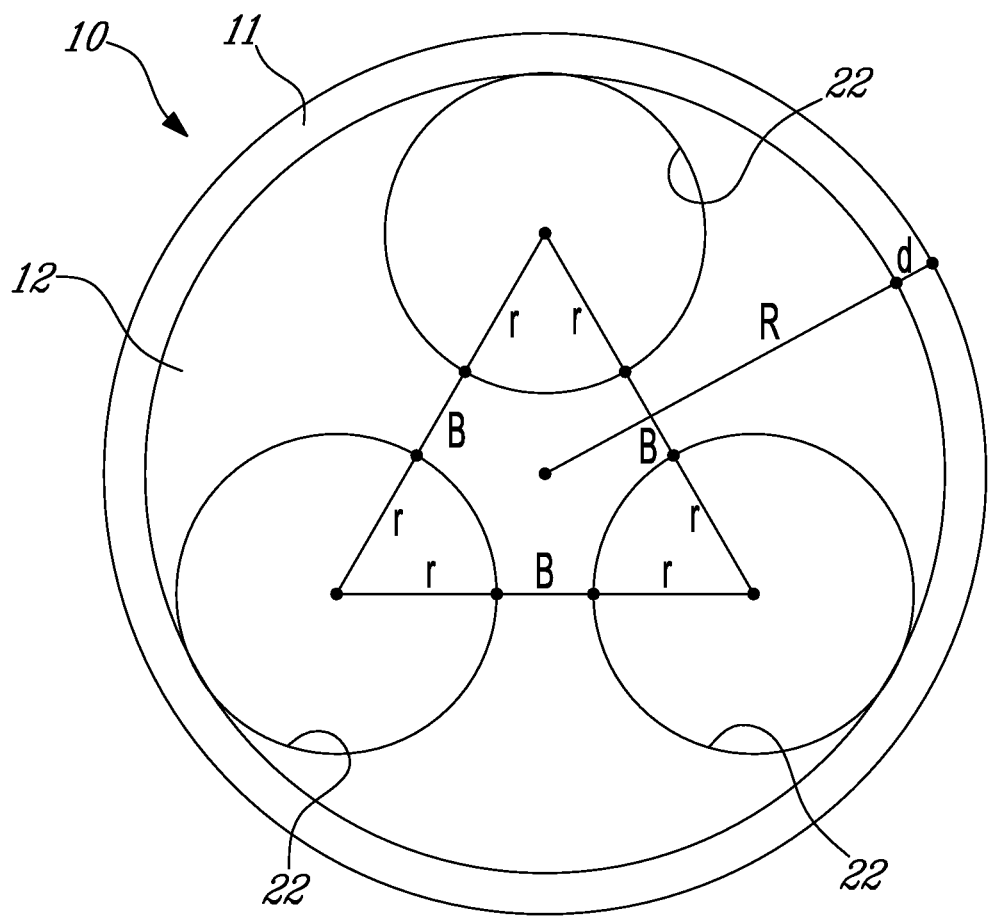
FIG. 6 is a reference sectional view of the drain catheters of FIGS. 1 and 4.

In FIGS. 5A to 5E, dimensions are provided as an example. These dimensions can be increased or reduced, proportionally to the outer diameter of the main proximal drain tube 11 of drain tubes 13. Referring to FIG. 6, various embodiments are provided with dimensions. These dimensions are provided as an example, and the drain catheters 10/10' should not be restricted to these dimensions, as other dimensions are also considered.

In accordance with a first embodiment, the drain tube 11 has an inner diameter 2 R of about 20 mm, with a thickness d of about 2 mm, for an outer diameter of about 24 mm. The nominal length of the drain tube 11 is up to 1 m. Still in the first embodiment, the outer diameter of the tube interface 12/12' is of about 20 mm (i.e., 2 R), while the canals 22 have a radius r of about 4 mm. The distance B between the canals 22 is about 2.4 mm. The length of the tube interface 12/12' is about 40 mm. Still in the first embodiment, the outer diameter of the distal tubes 13 is of about 8 mm (i.e., 2 r). The length of the distal tubes 13 is about 700 mm.

The inner diameter of the drain tube 11 may range between 10.0 mm and 25.4 mm. The other dimensions of the drain catheter 10/10' are generally proportional to that of the inner diameter of the drain tube 11. In accordance with a second embodiment, the drain tube 11 has an inner diameter 2 R of about 10 mm, with a thickness d of about 2 mm, for an outer diameter of about 14 mm. The nominal length of the drain tube 11 is up to 1 m. Still in the second embodiment, the outer diameter of the tube interface 12/12' is of about 10 mm (i.e., 2 R), while the canals 22 have a radius r of about 1.66 mm. The distance B between the canals 22 is about 2.44 mm. The length of the tube interface 12/12' is about 40 mm. Still in the second embodiment, the outer diameter of the distal tubes 13 is of about 3.3 mm (i.e., 2 r). The length of the distal tubes 13 is about 700 mm. In an embodiment, the outer diameter of the proximal drain tube 11 is greater than a sum of an outer diameter of two of the distal drain tubes 13.

It is observed that the tube interface 12/12' is arranged such that there is no increase in diameter from the distal tubes 13 to the main drain tube 11, the largest outer diameter being that of the main drain tube 11. Whether the main drain tube 11 actually enters the body or not, the arrangement of the figures allows to use a single suction port and a single tube (11), for two or more distal drains 13 located at different regions of a body cavity. This may result in increased coverage resulting in enhanced drainage.

What is claimed is:

1. A drain catheter comprising: a proximal drain tube having a proximal end adapted to outlet drained liquids and a distal end;
   a tube interface at a distal end of the proximal drain tube, the tube interface having at least two canals open to a distal end of the proximal drain tube, the at least two canals being in fluid communication with the proximal drain tube, a greatest outer diameter of the tube interface being smaller than an outer diameter of the distal end of the proximal drain tube; and
   at least two distal drain tubes each having a proximal end and a distal end, the proximal end of each said distal drain tube being connected to a corresponding one of the canals such that the distal drain tubes are each in fluid communication with the corresponding one of the canals, the distal end of each said distal drain tube being open to collect liquids, a lumen of the distal drain tubes being smaller than a lumen of the proximal drain tube, the at least two distal drain tubes diverging from the tube interface in a distal direction, the distal end of the at least two drain tubes being separated during use.

2. The drain catheter according to claim 1, wherein the tube interface is constituted of at least two body portions separable to provide access to the canals, the at least two body portions forming a cylindrical body with the at least two canals, the cylindrical body being received inside the distal end of the proximal drain tube, and the canals receiving therein the proximal ends of the at least two distal drain tubes, the cylindrical body sealing off interstitial space between an inner diameter of the proximal drain tube and an outer diameter of the at least two distal drain tubes.

3. The drain catheter according to claim 1, wherein the tube interface is constituted of a cylindrical body with the at least two canals and longitudinal slits to provide access to an interior of the at least two canals, the cylindrical body being received inside the distal end of the proximal drain tube, and the canals receiving therein the proximal ends of the at least two distal drain tubes, the cylindrical body sealing off interstitial space between an inner diameter of the proximal drain tube and an outer diameter of the at least two distal drain tubes.

4. The drain catheter according to claim 1, wherein the tube interface is made of silicone.

5. The drain catheter according to claim 1, wherein the proximal drain tube, the tube interface and the at least two distal drain tubes are an integrally molded single piece, with the tube interface transitioning from a geometry of the at least two distal drain tubes to the proximal drain tube with an edgeless outer surface.

6. The drain catheter according to claim 1, wherein an outer diameter of the proximal drain tube is greater than a sum of an outer diameter of two of the distal drain tubes.

7. The drain catheter according to claim 1, wherein each said distal drain tube has an elongated body of generally circular section, with at least two longitudinal channels extending toward the tube interface from the distal end of the distal drain tube to form elongated peripheral wall portions, and a core member inside each said distal drain tube to support the elongated peripheral wall portions.

8. The drain catheter according to claim 7, wherein each said distal drain tube comprises four of said longitudinal channels, and the core member is cross-shaped.

9. The drain catheter according to claim 8, wherein the core member inside each said distal drain tube extends into a corresponding one of the canals into the tube interface.

10. The drain catheter according to claim 7, wherein the longitudinal channels end proximally before reaching the tube interface, while the core member extends into the tube interface.

11. The drain catheter according to claim 7, wherein the core member inside each said distal drain tube extends into a corresponding one of the canals into the tube interface.

12. The drain catheter according to claim 1, comprising three of said distal drain tubes for one said proximal drain tube.

13. The drain catheter according to claim 1, wherein the at least two canals each have a substantially cylindrical shape from end to end of the tube interface.

14. The drain catheter according to claim 1, wherein each of the at least two distal drain tubes define a distal extremity of the drain catheter in use, each of the at least two distal drain tubes having an outer diameter less than 5.0 mm.

15. The drain catheter according to claim 1, wherein each of the at least two distal drain tubes has a constant diameter from its proximal end to its distal end.

* * * * *